United States Patent
Azarbarzin et al.

(10) Patent No.: US 9,084,628 B2
(45) Date of Patent: Jul. 21, 2015

(54) ENDOLUMINAL AND TRANSLUMINAL SURGICAL METHODS AND DEVICES

(71) Applicant: SurgiQuest, Inc., Milford, CT (US)

(72) Inventors: Kurt Azarbarzin, Fairfield, CT (US); Timothy J. Nolan, South Salem, NY (US); Ralph Stearns, Bozrah, CT (US); Daniel B. Jones, Wayland, MA (US)

(73) Assignee: SurgiQuest, Inc., Milford, CT (US)

( * ) Notice: Subject to any disclaimer, the term of this patent is extended or adjusted under 35 U.S.C. 154(b) by 0 days.

(21) Appl. No.: 13/666,231

(22) Filed: Nov. 1, 2012

(65) Prior Publication Data

US 2013/0060091 A1 Mar. 7, 2013

Related U.S. Application Data

(63) Continuation of application No. 12/148,234, filed on Apr. 17, 2008.

(51) Int. Cl.
| | | |
|---|---|---|
| *A61B 1/04* | (2006.01) | |
| *A61B 1/12* | (2006.01) | |
| *A61M 31/00* | (2006.01) | |
| *A61B 17/10* | (2006.01) | |
| *A61B 17/04* | (2006.01) | |
| *A61B 17/34* | (2006.01) | |

(Continued)

(52) U.S. Cl.
CPC ......... *A61B 17/3417* (2013.01); *A61B 1/00052* (2013.01); *A61B 1/018* (2013.01); *A61B 1/042* (2013.01); *A61B 17/22031* (2013.01); *A61B 17/3421* (2013.01); *A61B 17/00234* (2013.01); *A61B 17/3431* (2013.01); *A61B 17/3474* (2013.01); *A61B 19/38* (2013.01); *A61B 19/5212* (2013.01); *A61B 19/5225* (2013.01); *A61B 2017/003* (2013.01); *A61B 2017/00278* (2013.01); *A61B 2017/00398* (2013.01); *A61B 2017/00544* (2013.01); *A61B 2017/00867* (2013.01); *A61B 2017/00907* (2013.01); *A61B 2019/5217* (2013.01)

(58) Field of Classification Search
USPC ................. 600/104, 106, 114–116, 121–125, 600/154–159; 604/26, 43–45, 506–517; 606/139–151
See application file for complete search history.

(56) References Cited

U.S. PATENT DOCUMENTS

| 6,059,797 A * | 5/2000 | Mears ........................... 606/140 |
| 2005/0015043 A1 * | 1/2005 | Stubbs et al. ................... 604/26 |

(Continued)

FOREIGN PATENT DOCUMENTS

JP 2005245772 A * 9/2005 ............... A61B 1/00

*Primary Examiner* — Ryan Henderson
(74) *Attorney, Agent, or Firm* — Locke Lord LLP; Scott D. Wofsy; Arpita G. Buesing

(57) ABSTRACT

An access device adapted and configured to be inserted through a natural biological orifice, and related surgical methods are provided. The access device includes a body, a nozzle means and means for delivering a pressurized flow of fluid to the nozzle means. The body is configured and dimensioned to be inserted through a natural bodily orifice and has proximal and distal end portions and defines at least one lumen therethrough to accommodate passage of one or more surgical instruments. The nozzle means is operatively associated with the body for directing pressurized fluid into the lumen to develop a pressure differential in an area within a region within the lumen to form a fluid seal around the one or more surgical instruments passing therethrough.

14 Claims, 15 Drawing Sheets

(51) Int. Cl.
*A61B 1/00* (2006.01)
*A61B 1/018* (2006.01)
*A61B 17/22* (2006.01)
*A61B 17/00* (2006.01)
*A61B 19/00* (2006.01)

(56) References Cited

U.S. PATENT DOCUMENTS

2005/0107664 A1* 5/2005 Kalloo et al. ............... 600/115
2010/0261962 A1* 10/2010 Friedberg .................... 600/114

* cited by examiner

ENDOLUMINAL AND TRANSLUMINAL SURGICAL METHODS AND DEVICES

CROSS-REFERENCE TO RELATED APPLICATIONS

This application claims benefit of priority to U.S. Provisional Patent Application Ser. No. 60/959,811 filed Jul. 16, 2007 and U.S. Provisional Patent Application Ser. No. 60/923,832, filed Apr. 17, 2007, which applications are hereby incorporated by reference in their entirety.

BACKGROUND OF THE INVENTION

1. Field of the Invention

The present invention relates generally to surgical methods and devices therefor, including surgical access devices. Particularly, the present invention is directed to surgical access ports for use in endoluminal or transluminal procedures, such as through the human esophagus or lower gastrointestinal tract, and related methods.

2. Description of Related Art

A variety of devices are known in the art for assisting surgical procedures—including cannulas for accessing internal cavities of a patient, and other devices, such as endoscopes.

Endoscopy is a term for a range of medical procedures that allow a doctor to observe the inside of the body without performing major surgery. An endoscope (e.g., a fibrescope) is a long tube with a lens at the distal end and an eyepiece and/or camera at the proximal end. The end with the lens is inserted into a patient. Light is transmitted through the tube (via bundles of optical fibres) to illuminate the surgical site, and the eyepiece magnifies the area so the doctor can visualize the surgical site. Usually, an endoscope is inserted through one of the body's natural openings, such as the mouth, urethra or anus, but depending on the particular procedure, may require a small incision through the skin. Such procedures are often performed under general or local anesthetic. Specially designed endoscopes are used to perform simple surgical procedures, such as tubal ligation ("tying" of the female fallopian tubes); locating, sampling or removing foreign objects or tumors from the lungs or digestive tract; removal of the gallbladder; taking small samples of tissue for diagnostic purposes (biopsy).

A range of endoscopes have been developed for many parts of the body. Each has its own name, depending on the part of the body it is intended to investigate. For example, an arthroscope is inserted through a small incision to examine a skeletal joint. A bronchoscope is inserted down the trachea (windpipe) to examine the lungs. A colonoscope is inserted through the anus to examine the colon. A gastroscope is inserted down the esophagus to examine the stomach. A hysteroscope is inserted through the cervix to examine the uterus. A laparoscope is inserted through a small incision to examine the abdominal organs. A cystoscope is inserted via the urethra to examine the urethra and urinary bladder. Many of the foregoing procedures can be carried out with one or more instruments used in conjunction with an endoscope. Such procedures often also require an opening through which the endoscope and/or instruments can pass. Such working channels can be natural openings—e.g. the mouth and esophagus, or artificial openings such as an incision made in the abdomen of a patient.

Applicants recognize that current endoscopic systems suffer from various limitations, particularly when used in conjunction with certain medical procedures. Some endoscopes may be configured with an integral working channel. Such working channels are often small, and may or may not be suitable for a particular instrument to be inserted therethrough. Moreover, it can prove difficult to obtain good working instruments in very small sizes. Further, imaging through fibers can be limiting—often due to low resolution images. If an endoscope is provided with an imaging chip on a scope having a circular cross-section, this can restrict the size and quality of images obtained therefrom. Moreover, if insufflation is required for a particular procedure, insufflation through an endoscope is typically maintained with mechanical seals. Even state-of-the-art mechanical seals typically present difficulty for a surgeon due to substantial friction, which results in difficult manipulation and restricted instrument access.

Applicants recognize that with the foregoing problems in the art, there remains a need for improved visualization and access devices that allow for easier access and movement and better quality imaging. The present invention provides a solution for these problems.

SUMMARY OF THE INVENTION

The purpose and advantages of the present invention will be set forth in and apparent from the description that follows. Additional advantages of the invention will be realized and attained by the devices and methods particularly pointed out in the written description and claims hereof, as well as from the appended drawings. The present invention is directed to devices, as described hereinbelow, as well as to methods utilizing such devices.

To achieve these and other advantages and in accordance with the purpose of the invention, as embodied, the invention includes an access device adapted and configured to be inserted through a natural biological orifice is provided. The access device includes a body, a nozzle means and means for delivering a pressurized flow of fluid to the nozzle means. The body is configured and dimensioned to be inserted through a natural bodily orifice and has proximal and distal end portions and defines at least one lumen therethrough to accommodate passage of one or more surgical instruments. The nozzle means is operatively associated with the body for directing pressurized fluid into the lumen to develop a pressure differential in an area within a region within the lumen to form a fluid seal around the one or more surgical instruments passing therethrough.

In accordance with the invention, the body can be substantially rigid or substantially flexible, or include both rigid and flexible elements, as required. The access device can include at least one control element for manipulation of the curvature of the access device. Alternatively, two individual control elements can be used to control orthogonal motion—e.g., with respect to X and Y axes. Such control elements can further be provided in one or more opposing pairs. Such control elements can be, for example flexible or semi-rigid rods, wires or ribbons. Manipulation of the curvature of the entire access device can be controlled, or alternatively, the curvature of only the distal tip can be controlled, depending on the precise implementation.

One or more image sensors can be arranged in the distal end portion of the access device, which are adapted and configured to capture images of a region distal the distal end portion of the access device. If multiple image sensors are provided, they can facilitate stereoscopic imaging of the subject region. One or more working channels can be provided in the wall of the access device, and one or more of said working channels can be configured and adapted to provide irrigation to a surgical site. Alternatively or additionally, one or more of said working channels can be configured and adapted to provide drainage to a surgical site and one or more channels can be configured to allow a surgical instrument to pass therethrough.

One or more light sources can be arranged in the distal end portion of the access device, and adapted and configured to illuminate a region distal the distal end portion of the access device. Alternatively or additionally, illumination means can be provided in the wall of the access device.

Further, one or more guide elements adapted and configured to guide surgical instruments in the lumen of the access device can be provided. One or more pressure sensing channels can be arranged in the wall of the access device, and be configured and adapted to be in fluid communication with a surgical site.

Devices in accordance with the invention can be of any length desired or required. For example, the length of the body can be between about 30 cm and about 50 cm, depending on the precise application. A range of length between about 30 cm and 40 cm is particularly advantageous for a transesophageal access route for an endoluminal intra-gastric procedure—accessing a patient's stomach or duodenum. In alternate embodiments, the length of the body can be between about 40 cm and 50 cm, which range of length is particularly advantageous for transluminal access to internal organs via a trans-gastric route—that is, accessing a an organ through the wall of a patient's stomach. If desired, devices in accordance with the invention can be in the range of about 15 cm to about 20 cm for use as an anoscope and transanal access to the rectum, and can be up to about 160 cm in length for use as, or in conjunction with, a colonoscope, depending on the precise implementation. In accordance with one embodiment of the invention, a device provided with integral optics and illumination is between about 90 cm and 130 cm in length, preferably about 110 cm in length. Internal diameters of access devices in accordance with the invention can be any size that is practical for the application, but preferably range between about 10 mm and 20 mm, and in a preferred embodiment, between 15 mm and 18 mm.

Access devices in accordance with the invention can further comprise an integral image display provided in the proximal end portion thereof.

In accordance with another aspect of the invention, an insertion device is provided for inserting access devices in accordance with the invention. Such insertion devices can have a tip portion to facilitate insertion of the access device through a natural orifice. The tip can taper to a substantially blunt end and/or can include a dilating element. The tip portion can include at least one transparent region. The insertion device can be provided with illuminating means for illuminating a region distal the insertion device. Also, the insertion device can be configured and adapted to interface with an endoscope to facilitate guidance of the user during insertion. The insertion device can further include an integral lens arranged in a distal end portion thereof.

Further in accordance with the invention, a method of accessing an internal region of a body is provided. The method includes inserting through a natural body orifice an elongated body having longitudinally opposed proximal and distal end portions. The body defines at least one lumen configured and dimensioned to accommodate passage of one or more surgical instruments. The body further includes nozzle means operatively associated with the body for directing pressurized fluid into the lumen to develop a pressure differential in an area within a region within the lumen to form a fluid seal around the one or more surgical instruments passing therethrough. The method further includes the steps of delivering pressurized fluid to the nozzle means to create said pressure differential; and inserting one or more surgical instruments through the body to access the interior of the body.

In accordance with another aspect of the invention, an access device is provided which is adapted and configured to be inserted through an orifice. The access device includes a body, a nozzle means, means for delivering a pressurized flow of fluid to the nozzle means and at least one control element. The body is configured and dimensioned to be inserted through an orifice and has proximal and distal end portions and defines at least one lumen therethrough to accommodate passage of one or more surgical instruments, and is flexible in at least one region. The nozzle means is operatively associated with the body for directing pressurized fluid into the lumen to develop a pressure differential in an area within a region within the lumen to form a fluid seal around the one or more surgical instruments passing therethrough. The at least one control element is arranged within the body and is adapted and configured to effect a change in curvature of the at least one flexible region of the body. In accordance with the invention, the orifice can be a natural biological orifice, or alternatively can be formed from an incision made in the patient.

In accordance with still another aspect of the invention, a method for performing a cholecystectomy is provided. The method includes the steps of inserting a first access device through the esophagus of a patient and into the stomach, penetrating the stomach wall and extending the first access device through the stomach wall, inserting a second access device through the umbilicus of the patient, inserting an endoscope through the first access device, retracting the gallbladder, exposing the cystic duct and cystic artery, applying at least two clips on each of the cystic duct and artery, transecting each of the cystic duct and artery, dissecting and removing the gallbladder from the liver bed, and removing the gallbladder.

It is to be understood that both the foregoing general description and the following detailed description are exemplary and are intended to provide further explanation of the invention.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein:

FIG. 1b is a proximal end view of the embodiment of FIG. 1a;

FIG. 1c is a distal end view of the embodiment of FIG. 1a;

FIG. 4b is a distal end view of the access device of FIG. 4a;

FIG. 13a is a partial view of the distal end of a further embodiment of an access device constructed in accordance with the invention having internal steering elements;

FIG. 13b is a cutaway view of the distal end of the access device of FIG. 13a;

DETAILED DESCRIPTION OF THE PREFERRED EMBODIMENT

Reference will now be made in detail to select embodiments of the invention, examples of which are illustrated in the accompanying drawings.

The devices and methods presented herein may be used as surgical access ports, particularly for endoluminal or transluminal medical procedures. The devices described and set forth herein can incorporate any feature from the following U.S. Patent applications and patents, which are each incorporated herein by reference in their entirety: U.S. patent application Ser. No. 11/517,929, filed Sep. 8, 2006 (U.S. Patent Publication No. US 2007/0088275, published Apr. 19, 2007), which is a continuation-in-part of U.S. patent application Ser. No. 10/776,923, filed Feb. 11, 2004 (now U.S. Pat. No. 7,338,473), which is a continuation-in-part of U.S. patent application Ser. No. 10/739,872, filed Dec. 18, 2003 (now U.S. Pat. No. 7,285,112), which is a continuation-in-part of U.S. patent application Ser. No. 10/441,149, filed May 17, 2003 (now U.S. Pat. No. 7,182,752). Each of the foregoing applications also claims priority to U.S. Provisional Application Ser. No. 60/461,149, filed Apr. 8, 2003, which itself is also hereby incorporated by reference in its entirety. The devices described and set forth herein can further incorporate any feature from U.S. patent application Ser. No. 11/544,856 (U.S. Patent Publication No. US 2008/0086167), and U.S. Provisional Application Ser. No. 60/850,006 both filed Oct. 6, 2006, which are also incorporated herein by reference in their entirety.

Figure 1A:
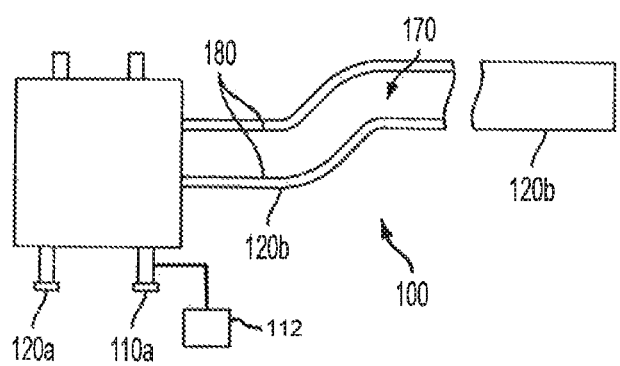
FIG. 1a illustrates a first embodiment of an access device in accordance with the invention, having a generally elliptical cross-section.
Figures 1B, 1C:
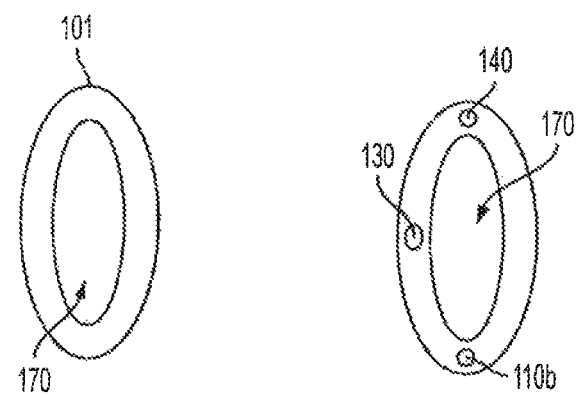

FIGS. 1a-1c illustrate a first embodiment of an access device 100 in accordance with the invention. This embodiment has a generally elliptical cross-section, as can be seen at its proximal end 101 (FIG. 1b). Further, this access device 100, as embodied in FIGS. 1a-1c, is sufficiently flexible to navigate a natural body orifice through which it is intended to be inserted. The access device 100 includes an insufflation input 120a, and a pressure sensing channel having proximal and distal openings 110a, 110b, respectively. A pressure sensing device 112 (shown schematically) is in communication with the pressure sensing channel. The pressure sensing device 112 can be a surgical insufflator, electronic pressure transducer or a diaphragm valve, for example. The body of the access device 100 includes a lumen 170, and can be embodied so as to include manipulating elements 180, such as wires, to effect curvature of the access device 100, when desired. An image sensor 130 may be provided at the distal end region, as may be at least one light source 140. In this embodiment it is contemplated that the at least one light source, may be one or more light-emitting diodes (LEDs), and that one or more CMOS, CCD or other small image sensors may be mounted at the distal end of the device and used as image sensors. Images can be transmitted to the external environment through conductive elements provided on or within the access device 100, or can be provided wirelessly, such as by radio frequency transmission to a receiver. Alternatively, it is contemplated that the access device might not contain integrated optics and that known types of viewing devices may be inserted through the central lumen or a working channel of the access device for viewing purposes.

Devices in accordance with the invention can be of any length desired or required. For example, the length of the body can be between about 30 cm and about 50 cm, depending on the precise application. A range of length between about 30 cm and 40 cm is particularly advantageous for a transesophageal access route for an endoluminal intra-gastric procedure. In alternate embodiments, the length of the body can be between about 40 cm and 50 cm, which range of length is particularly advantageous for transluminal access to internal organs via a trans-gastric route—that is, accessing a an organ through the wall of a patient's stomach. If desired, devices in accordance with the invention can be in the range of about 15 cm to about 20 cm for use as an anoscope and transanal access to the rectum, and can be up to about 160 cm in length for use as, or in conjunction with, a colonoscope, depending on the precise implementation. In accordance with one embodiment of the invention, a device provided with integral optics and illumination is between about 90 cm and 130 cm in length, preferably about 110 cm in length. Internal diameters of access devices in accordance with the invention can be any size that is practical for the application, but preferably range between about 10 mm and 20 mm, and in a preferred embodiment, between 15 mm and 18 mm.

Additional features that can be incorporated into access devices in accordance with the invention include, but are not limited to having an outer cross-sectional shape ranging from circular, through an elliptical shape to near linear in shape.

With respect to the embodiment of FIGS. 1a-1c, one or more fluid seals 120b are provided to seal between instruments passing through the lumen 170, and the wall of the lumen, in order to maintain pressure within an operative space. Various embodiments of access devices having fluid seals (or alternatively "air seals" or "pneumatic seals") are set forth in the documents referenced above. Although mechanical sealing can additionally be incorporated into different embodiments of access devices described therein, as well as into those described in connection with the present invention, such mechanical seals can equally be absent, allowing substantially unencumbered movement of instruments through and within such access devices.

In accordance with the present invention the access device 100 of FIG. 1 or any access device set forth herein can be provided with a fluid seal, as described in the documents referenced above. The subject access devices can further include one or more of the following features: one or more endoscopes; one or more working channels; illumination capability; and/or the capability to be steered by a user. Incorporation of non-mechanical seals into endoluminal and transluminal access devices in accordance with the invention can allow for easier, safer procedures as well as new approaches to procedures.

Fluid seals in accordance with the invention can be embodied in a variety of suitable manners. Nozzles can be provided that are substantially annular in configuration, or alternatively, if desired, a plurality of discrete nozzle apertures can be defined in place one such annular nozzle. These discrete nozzle apertures can be arranged as necessary, about the wall of the access device, to form an effective barrier to proximal egress of insufflation gas from a surgical site. Such discrete nozzles can each be substantially round in shape, or alternatively can be oblong or another shape. The nozzles can be placed at regular intervals about the circumference of the lumen, can extend part way around, or can be spaced from each other in groups. If turbulence is desired, surface features such as protrusions, vanes, grooves, surface texture can be added in the path of fluid flow, as desired. Further, one or more nozzles or groups of nozzles can be provided in access devices in accordance with the invention, with such nozzles being located in one region, or in a plurality of regions along the length of the access device.

Figure 2A:
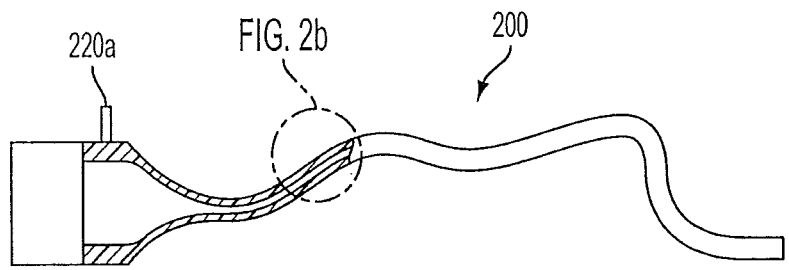
FIG. 2a illustrates a further embodiment of an access device in accordance with the invention, in which the wall of the device houses additional working channels.
Figure 2B:
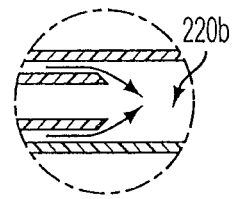
FIG. 2b is a cutaway view of a portion of the access device of FIG. 2a, illustrating a fluid seal in accordance with the invention.
Figure 2C:
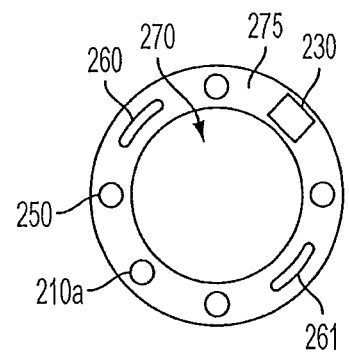
FIG. 2c is a distal end view of the embodiment of FIG. 2a, illustrating working channels and other features.

FIGS. 2a-2c illustrate a further embodiment of an access device 200, in accordance with the invention. The access device 200 includes an insufflation fluid input 220a, which is in fluid communication with a fluid seal 220b. The fluid seal may be positioned within the proximal housing of the device or may be positioned at any desired location between the proximal housing and the distal tip of the device. A lumen 270 serves as a working channel for passage of surgical instruments and the like, and is defined by the wall 275 of the access device 200. The wall 275 itself also houses additional working channels, such as an irrigation port 260, drainage port 261 and pressure sensing port 210a. Additional ports can be used for additional functions, as desired or required. Optionally, illumination can be provided by way of one or more light sources, which can be provided directly in the wall 275, or whose light can be transmitted through the wall 275, to the distal end thereof by one or more fiber optic elements 250.

Further, one or more optional image sensors 230 can be provided in the wall 275 in order to capture images of a surgical site.

In accordance with the invention, the foregoing and following embodiments can be flexible or rigid, as desired or required. Further the foregoing and below-described access devices allow a user to pass a plurality of surgical instruments through a natural lumen into the human body. Such natural openings include, for example, the mouth and esophagus, the anus and rectum or vagina.

Entrance through such natural openings can provide access into the digestive tract without surgical incisions penetrating the external abdominal wall. Furthermore, gastrointestinal pressures can be maintained within the organ(s), such as the stomach, without any interference with inserted instruments which would typically be caused by mechanical seals used in a typical endoscope, colonoscope, trocar, cannula or other access systems. Moreover, manipulation of surgical instruments is less encumbered, as compared with more conventional devices having mechanical seals. The subject access devices suffer less from frictional resistance between inserted instruments and the access device. Reducing such interference and friction is advantageous, and may reduce torque and other forces transmitted from the inserted instrument through the access device to surrounding tissue, which can cause trauma and prolong healing and recovery. The access device may also allow crossing of paths of the inserted instruments, as when switching hands, without having to retract and then reinsert an instruments.

Endoscopic surgical or exploratory access via a transesophageal or transanal route can be intraluminal—that is, it can be used for accessing the natural lumen itself (e.g., the esophagus, stomach, rectum, colon), or can be transluminal, that is—used to access other anatomy through the wall of such structures. Such an approach can be referred to as Natural Orifice Transluminal Endoscopic Surgery™ ("NOTES"). Such access can allow for imaging, insertion of one or more surgical instruments, removal of a tissue specimen, or insufflation of the lumen (e.g., the stomach). For example, access to a patient's peritoneum can be achieved through an internal endoluminal route. Moreover, insufflation of the peritoneum is possible using access devices in accordance with the invention. The following is a sample list of minimally-invasive procedures that can be accomplished by surgeons operating through access devices as described herein:

Endoluminal Access to the Upper GI Tract
    Reflux procedures, such as fundoplication
    Obesity procedures, such as gastric restriction
    Diabetes procedures such as duodenal bypasses
    Gastric Tumor Removal
Endoluminal Access to the Lower GI Tract
    Tumor removal
    Diverticulum removal, repair
Transluminal Access Through Esophagus, Rectum or Vagina
    All current abdominal and pelvic surgery such as:
    Gallbladder
    Appendectomy
    Ovarian cysts
    Oophorectomy
    Sterilization
    Hernia repair Devices in accordance with the invention can allow, in general, for new approaches to accessing anatomy. Any instrument inserted through the lumen of an access device equipped with one or more fluid seals in accordance with the invention will experience markedly reduced frictional resistance, due to replacement of mechanical seals with fluid seals.

It may, at times, prove useful to include one or more mechanical valves, such as for example a duckbill valve or other so-called "zero seal" intended to seal the access device when no instrument is inserted therethrough. However, typically the number of such valves will be reduced if not eliminated, for every fluid seal that is used. Without mechanical seals protruding into a lumen of access devices in accordance with the invention, more space for instruments is available, while free insertion and movement of the instruments is not hampered by mechanical seals.

Further, gas, such as carbon dioxide, can be supplied to such fluid seals in a continuous manner—thereby insufflating an operative space while also sealing the operative space. Such a continuous flow of insufflation gas is distinct from prior systems, in that prior insufflation technologies operate in a cyclic manner—alternately insufflating and sensing pressure. Such systems do not allow for insufflation when pressure is being sensed. A further advantage to access devices in accordance with the invention, is that maintaining a pressure barrier in an access device, between an insufflated space and the surrounding environment without the use of elastomeric seals provides the capability for safe relief from pressure buildup from any possible system failures or sources of additional pressure. Additionally, bucking is reduced when operating using devices in accordance with the invention. Bucking is the phenomenon where a patient tightens his diaphragm while his abdomen is insufflated. This tightening dramatically increases pressure within the abdomen. Further, if used in laparoscopic procedure, fluid seals incorporated with devices constructed in accordance with the invention all use of open type instrumentation.

Additionally, access devices in accordance with the invention allow for more freedom in instrument design. Because contact seals are not required, instruments inserted through access devices in accordance with the invention do not need to conform to the shape and size of such mechanical seals. Accordingly, instruments having a non-symmetrical shape can be used, which may be more efficient and cost-effective, and multiple instruments can be inserted simultaneously to improve manipulation through the access device. Advantageously, the absence of mechanical seals reduces the likelihood of smudging of optical components of surgical instruments inserted through access devices constructed in accordance with the invention.

Moreover, devices in accordance with the present invention can be provided with various cross-sectional shapes, including, but not limited to circular, elliptical, or as set forth above, cross-sectional shapes that approach a linear morphology when not in use. If embodied in an elliptical shape, access devices in accordance with the invention advantageously allow insertion of instruments of various sizes, such as instruments having an oblong cross-section. An elliptical cross-section can also allow for insertion of the access device in regions of the anatomy that would otherwise not allow insertion of an access device having a round cross-sectional shape.

Surgical instruments that can be used through access devices in accordance with the invention include, but are not limited to rigid or flexible versions of the following, depending on the procedure: graspers, scissors, snares, staplers, ultrasonic imaging devices, ultrasonic cutting and/or coagulating devices, vessel sealing devices, RF devices, microwave energy delivery devices glue delivery devices and suturing devices.

Access devices in accordance with the invention can further incorporate various imaging technologies. One or more image sensors can be utilized for image acquisition, which sensors can be incorporated into an access device, for example at or near the distal end thereof. Alternatively, standard fiber optic imaging technology may be inserted through the fluid seal or may be incorporated into a wall of the access device, such that an objective (lens) is at the distal end portion of the access device, and an image sensor and/or eyepiece is provided elsewhere, such as at the proximal end thereof. Such imaging devices can be embodied so as to obtain still images, but video images can alternatively or additionally be obtained to allow for real-time guidance of a procedure, and can allow for guidance during insertion of the access device itself. Additionally, illumination can be provided in the subject access devices in the form of integrated fiber-optics, connected to an external light source and/or integrated sources of light, such as LEDs (light-emitting diodes) integrated into the distal end portion of the access device. Capability for infrared imaging for diagnostic purposes can further be provided, in the form of an optical sensor capable of capturing light in the infrared region, and additionally, if needed, an infrared light source.

Figure 3A:
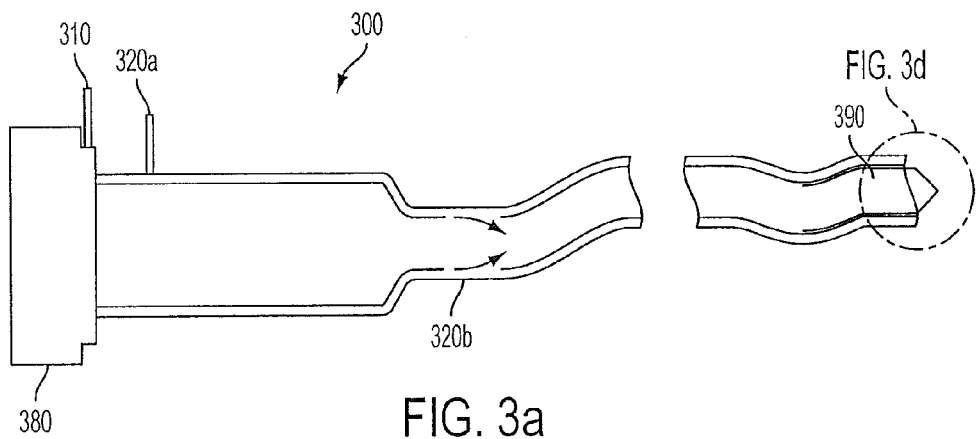
FIG. 3a illustrates an access device in accordance with the invention, which is flexible and manipulable, in which instrument guides can be provided integrally with the access device, or can be provided in an attachable cap.
Figure 3B:
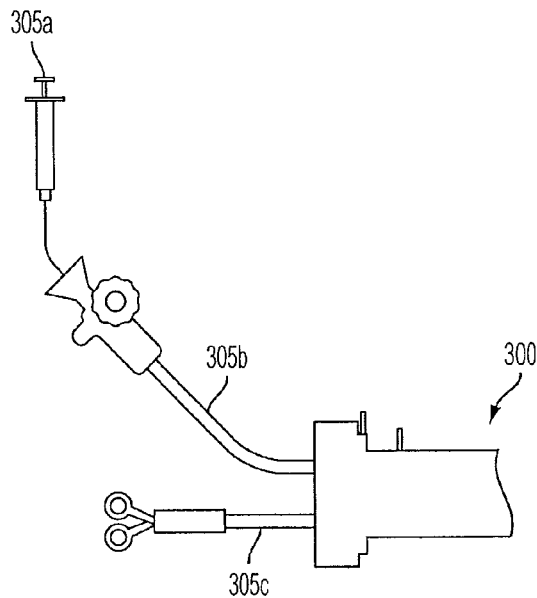
FIG. 3b is a partial view of the access device of FIG. 3a, illustrating surgical instruments inserted through the access device.
Figure 3C:
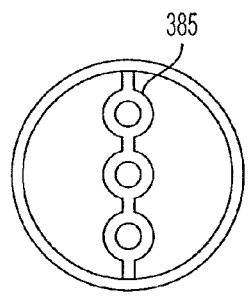
FIG. 3c is a proximal end view of the access device of FIG. 3a, illustrating an instrument guide provided therewith.
Figure 3D:
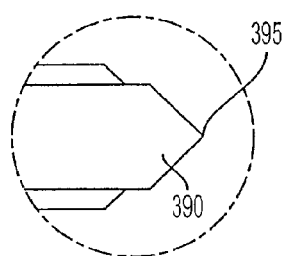
FIG. 3d is a partial view of the distal end of the access device of FIG. 3a, illustrating an insertion device inserted therethrough.

FIGS. 3a-3d illustrate a surgical access device 300 in accordance with the invention, which is flexible and manipulable, as with foregoing embodiments. One or more fluid seals 320b are provided therein, to which fluid (such as compressed air or inert gas, or in the case of arthroscopic or other surgery which utilizes liquid, saline or other suitable biocompatible liquid) is supplied via a fluid input 320a. A sensing input 310 is also provided, as described above in connection with other embodiments. If desired, instrument guides 385 (shown in the end view of FIG. 3c) can be provided integrally formed with the access device 300, or in the form of an attached cap 380 (FIG. 3a). As shown in FIG. 3b, surgical or exploratory instruments 305a, 305b, 305c pass through the guides 385, and thereby are prevented from moving undesirably, or unnecessarily interfering with one another.

Further in accordance with the invention, an insertion device 390 can be provided, which is inserted into the access device 300, prior to insertion in a patient. The insertion device 390 includes a tip 395, which facilitates insertion into a patient. Tip 295 may be blunt or sharp, rounded or pointed or such other configuration as appropriate for the intended insertion. Tip 395 also may be transparent to provide optical viewing during or after insertion.

Figure 4A:
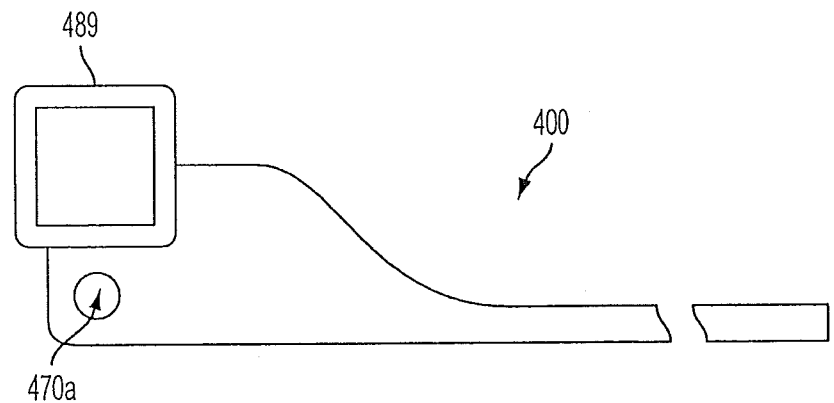
FIG. 4a illustrates an access device in accordance with the invention having a proximal display, such as an LCD display.
Figure 4B:
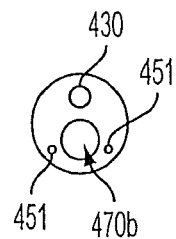

As illustrated in FIG. 4a, a proximal display 489, such as an LCD display, can be provided with access devices in accordance with the invention, such as access device 400 of FIGS. 4a and 4b. Such displays 489 can be integrated with respective access devices, or can be attached thereto in order to provide optimum viewing nearer the location in which the procedure is taking place, rather than on a display mounted far from the operating table. Such displays can provide high resolution direct images of the anatomy. In the embodiment of FIGS. 4a and 4b, the display 489 receives images from an image sensor 430 arranged in the distal end region of the access device 400. If desired, video signals from the image sensor 430 can be additionally output to display monitors by one or more wired and/or wireless connections. Of course, images may alternatively or additionally be displayed on a traditional monitor in the vicinity.

As best seen in FIG. 4b, illumination elements 451 may also be provided at the distal end region of the access device 400, and can include light sources, such as light-emitting diodes (LEDs) or alternatively or additionally, fiberoptic conduits that deliver light from an external light source. It is preferable, generally, that such illumination elements 451 be capable of providing bright, controllable illumination and be relatively small in size. As can be seen in FIG. 4b, the foregoing elements can be provided directly in a wall of the access device 400, which has a lumen 470, running therethrough, with openings 470*a* (FIG. 4*a*), 470*b* at proximal and distal ends of the access device 400, respectively.

The nature of access devices in accordance with the invention, particularly because fluid seals can be integrated therewith, allows the ability to use new flexible instruments of different shapes, geometries and mechanics. Such instruments might otherwise not be satisfactorily sealable with conventional sealing techniques. The absence of mechanical seals also can allow for passage of instrument drive and steering mechanisms, as well as for tissue manipulation, repair and/or retrieval.

Figure 5:
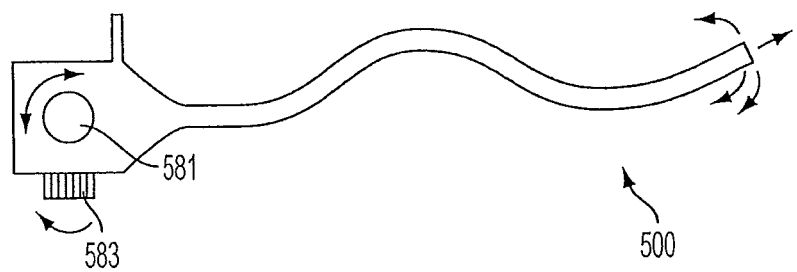
FIG. 5 illustrates a further embodiment of an access device in accordance with the invention, including control knobs which manipulate control elements provided within the access device.

FIG. 5 illustrates a further embodiment of an access device 500 in accordance with the invention. The access device 500 includes control knobs 581, 583, which manipulate control elements provided within the access device 500. When the control elements are placed in tension, the access device will tend to bend toward that control element. Conversely, when a control element is placed in compression, the access device 500, will tend to bend away from that control element. In the embodiment of FIG. 5, two controls 581, 583 control bending of the access device in two orthogonal directions, such as "X" and "Y" in a Cartesian coordinate system.

Figure 6:
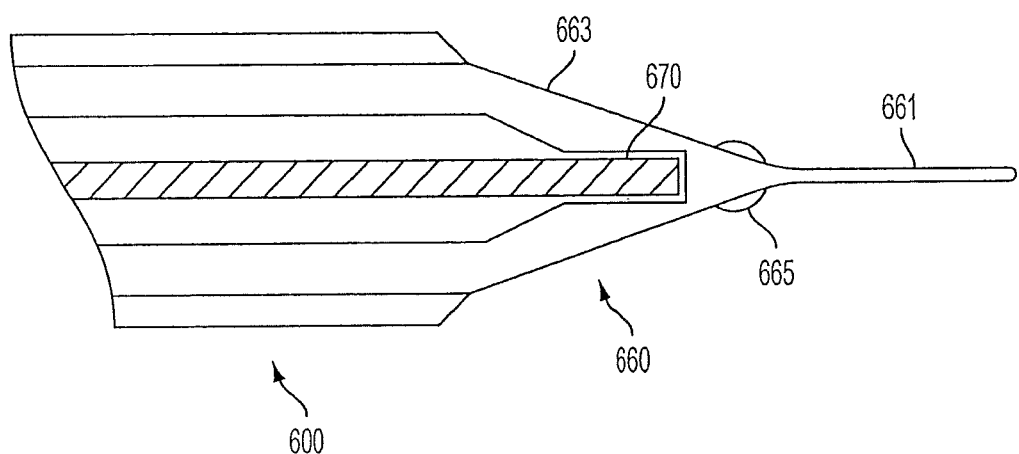
FIG. 6 is an enlarged cross-sectional view of a distal end portion of an access device in accordance with the invention, through which an insertion device has been inserted.

FIG. 6 is an enlarged cross-sectional view of a distal end portion of an access device 600, in accordance with the invention, through which an insertion device 660 has been inserted. The insertion device 660 may receive an endoscope 670 therethrough, which views the insertion site through one or more transparent windows or lenses 665. The lenses 665 can also be adapted to provide illumination to the insertion site. In this embodiment, the insertion device 660 may terminate in an elongate tip 661, which may facilitate dilation of a natural orifice through which the insertion device 660 and access device 600 assembly pass during insertion. Further, the contour 663 of the insertion device provides a relatively smooth transition to the diameter of the access device 600 from that of the tip 661.

Figure 7A:
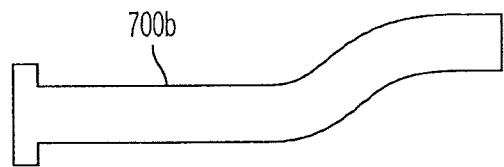
FIG. 7a illustrates a flexible access device, that is particularly configured and adapted for transanal insertion.
Figure 7B:
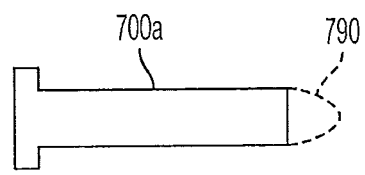
FIG. 7b illustrates a rigid access device that is particularly configured and adapted for transanal insertion.
Figure 7C:
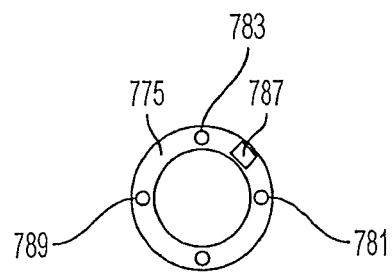
FIG. 7c is a distal end view of the access devices of FIGS. 7a and 7b.
Figure 7D:
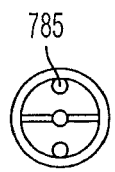
FIG. 7d is a proximal end view of the access devices of FIGS. 7a and 7b, illustrating instrument guides provided thereon.

FIGS. 7*a*-7*d* illustrate rigid and flexible access devices 700*a*, 700*b*, respectively, that are particularly configured and adapted for transanal insertion into the rectum of a patient. Features for these embodiments can be any of those set forth in connection with foregoing embodiments, including but not limited to use with an insertion device, incorporation of one or more fluid seals or insufflation means and/or steerability (in the case of flexible access devices). Further, as illustrated in FIG. 7*d*, which is a proximal end view of a cap for attachment to the access device 700*a*, 700*b*, instrument guides 785 can be provided. As best seen in the distal end view of FIG. 7*c*, irrigation channels 781, illumination capability 783, visualization components, such as one or more image sensors 787, or fiber optics to allow image transmission, and drainage capacity, such as in the form of drainage channels 789 can be incorporated. The foregoing elements can be arranged within the wall 775 of the access devices 700*a*, 700*b*, as with the embodiment described in connection with FIGS. 2*a*-2*c*, for example. Additionally, an insertion device 790 can be utilized to facilitate insertion into the body of a patient.

Figure 8:
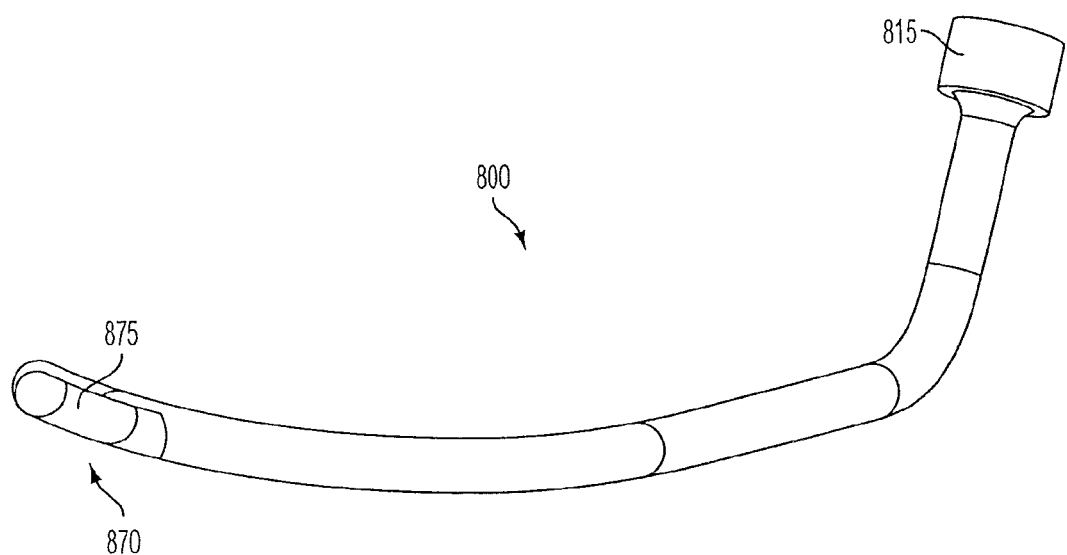
FIG. 8 is a side view of a further embodiment of an access device constructed in accordance with the invention having a distal end with open distal side portion.

FIG. 8 is a side view of a further embodiment of an access device 800 constructed in accordance with the invention. The access device 800 has a distal end 870 with open distal side portion 875. This embodiment allows instrumentation to be oriented to act on the side as an alternative to or in addition to through a distal end aperture. This arrangement is particularly advantageous when performing a procedure on the wall of a passage, such as the esophagus, stomach or duodenum, for example. A wall of such passage can be sucked via vacuum or pulled by mechanical means into contact with the access device 800 to facilitate a procedure. When in contact with the access device 800, steps including cutting, stapling and removal of tissue can be carried out. Vacuum can be applied in a number of ways, in accordance with the invention. Preferably, suction is applied directly through the access device 800. A single pump can be provided, which is adapted and configured to both provide insufflation pressure to the access device 800 and to provide suction to the access device 800. Use of a single pump allows for more streamlined surgical equipment and controls—reducing unnecessary clutter in the operating room and reducing cost by obviating a second pumping device. Naturally, if desired, separate pumps can be connected to the access device 800, and selectively activated in order to switch between insufflation and suction. Alternatively still, a secondary suction device can be utilized—either inserted through a central internal lumen of the access device 800 or external thereto.

Figure 9:
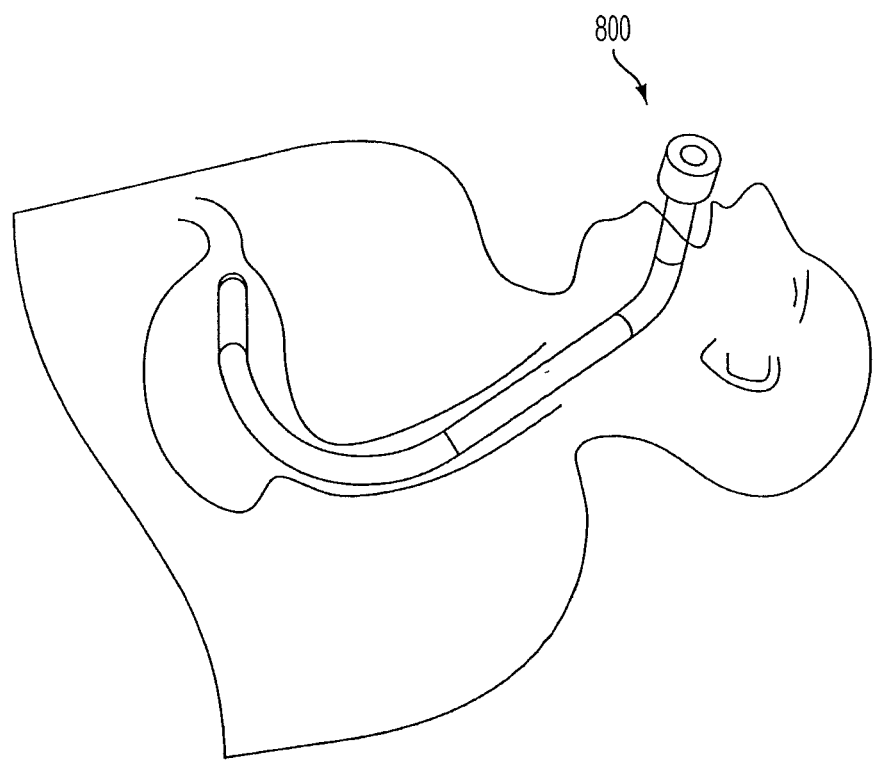
FIG. 9 is an illustration of the access device of FIG. 8 inserted through a patient's esophagus into the stomach.

Additionally, the access device 800 can be flexible to allow manipulation through the anatomy of a patient, as seen in FIG. 9. Moreover, the overall shape of the access device 800 can be preformed, as illustrated, so that the device has a tendency to revert to a shape that facilitates insertion and/or comfortable retention in the patient. The entire access device 800, or a portion thereof, such as the distal end portion, can be steerable to aid insertion of the access device and procedures performed therewith.

A fluid seal can be provided in the proximal end portion 815 of the access device 800, or additionally or alternatively at one or more other locations throughout the length of the access device 800.

Figure 10:
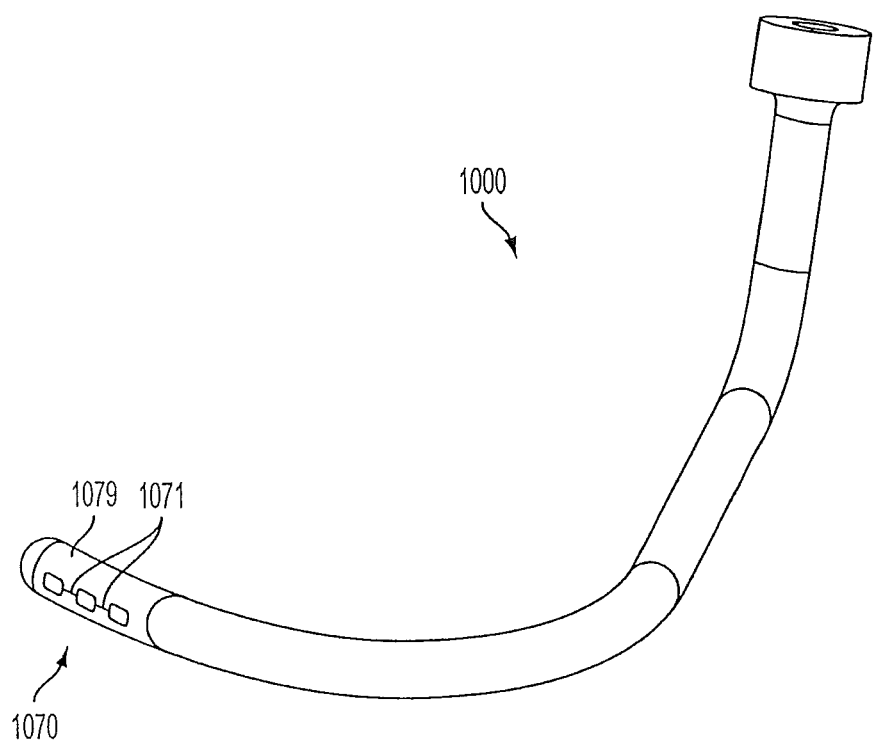
FIG. 10 is a side view of another embodiment of an access device constructed in accordance with the invention, with a distal end having a side-grasping feature with undulating grasping elements.
Figure 11:
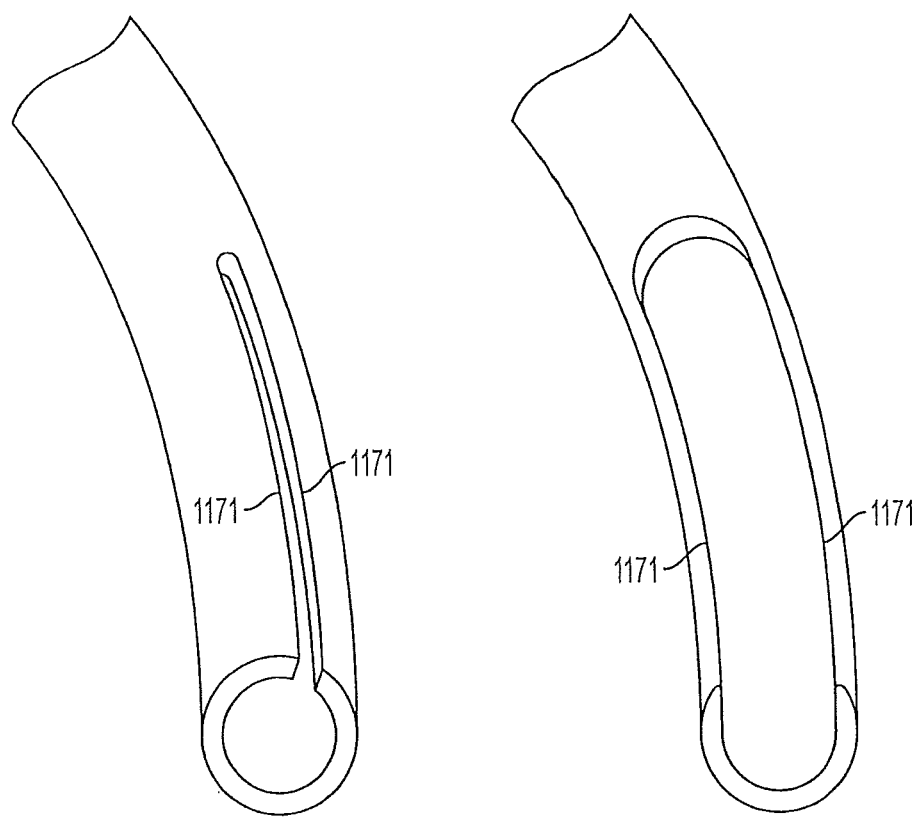
FIG. 11 is a partial view of the distal end of a variation of the embodiment of FIG. 10, with straight grasping elements.

FIG. 10 is a side view of another embodiment of an access device 1000 constructed in accordance with the invention. The access device 1000 is similar to that of FIGS. 8 and 9, but includes at its distal end 1070, a side-grasping feature with undulating grasping elements 1071. Alternatively, the side-grasping elements can be straight grasping elements 1171 as illustrated in FIG. 11.

Figure 12:
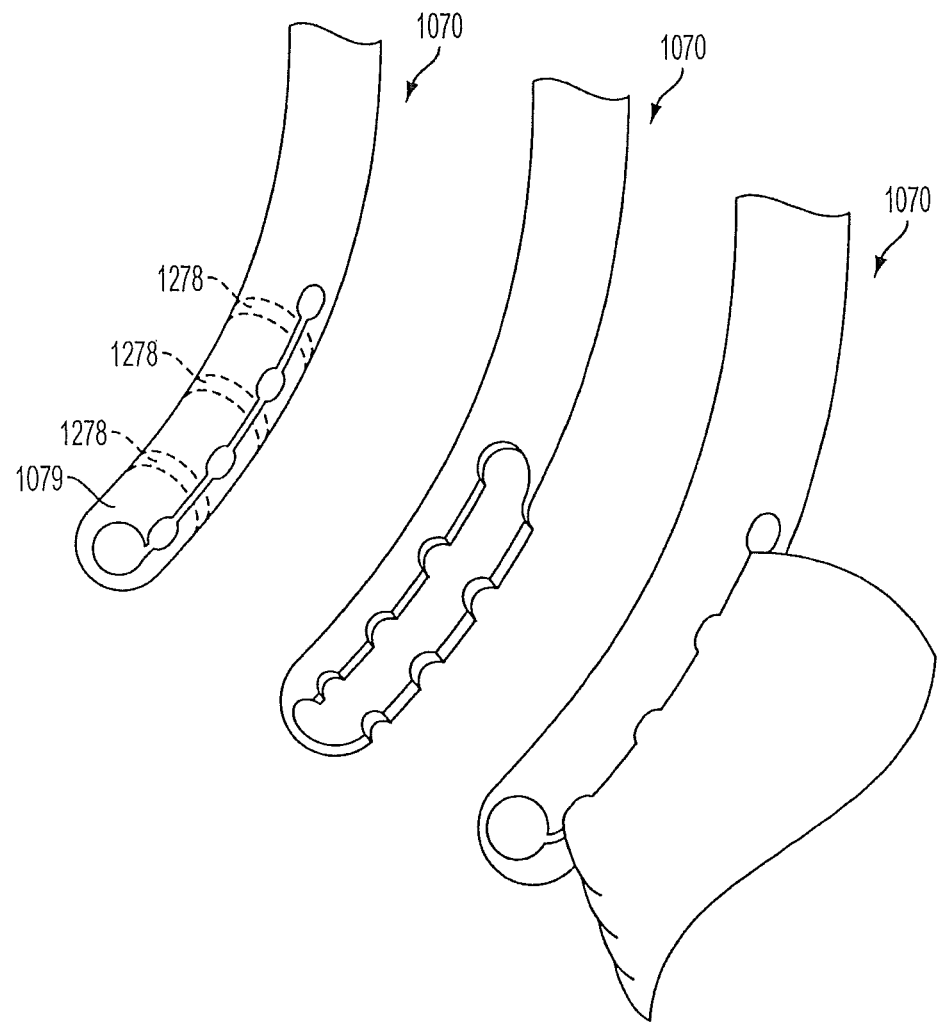
FIG. 12 illustrates three stages of an example procedure utilizing the access device of FIG. 10.

FIG. 12 illustrates the side grasping elements in closed, open and grasping positions, respectively. The grasping elements can be used to engage a wall of a passage, internal organ or other element, for example, to move the wall or steady the wall for another step, such as a puncture or incision. Actuation can be effected in any suitable manner. In accordance with one aspect of the invention, tension within the wall 1079 of the distal end 1071 is adjusted to effect closure or opening of the grasping elements 1071. Such tension can be adjusted by way of, for example, shape-memory alloy ribs 1278 arranged within the wall of the distal end 1070. Such ribs 1278 can have a first shape at normal room and/or body temperatures. The ribs 1278 can be electrically connected to a power source, such that when voltage is applied, resistive heating of the ribs 1278 effects a change in shape of the ribs to a second shape. Depending on the desired implementation, the normal state of the ribs can be open or closed.

Alternatively, the grasping elements 1071 can be actuated by providing one or more control elements (e.g., wires) terminating in a plurality of ends that terminate in or near the grasping elements 1071, within the wall 1079 of the distal end 1071. Accordingly, applying compression to such control cables will cause the grasping elements to close.

Figures 13A, 13B:
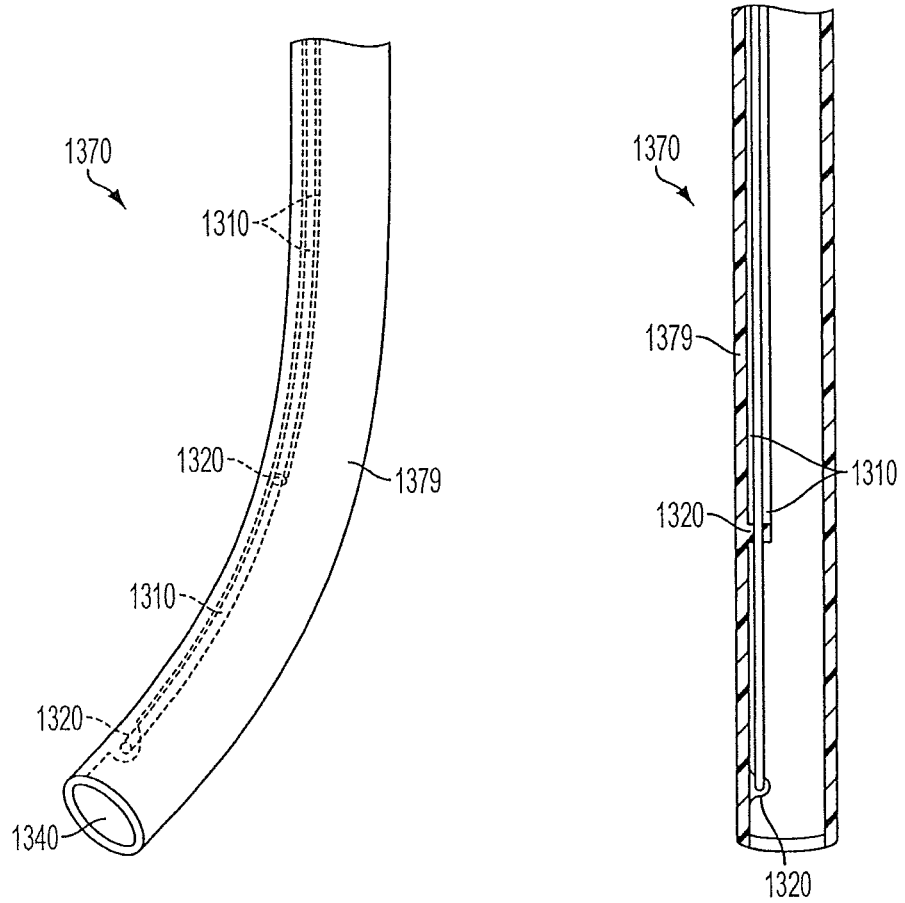

FIGS. 13*a* and 13*b* illustrate a distal end portion 1370 of a surgical access device constructed in accordance with the invention having a steerable distal end portion 1370. Control elements 1310, such as wires are provided within or adjacent the wall 1379 of the access device. The control elements 1310 are anchored in one or more locations 1320 to the wall of the access device. Although illustrated within the lumen 1340 of the access device, the control elements 1310 are provided with in the wall 1379. Tension applied to one or more control elements 1310 effects a change in curvature of the distal end portion 1370. In conjunction with applied rotation to the entire access device by a surgeon, navigation through the patient's anatomy is facilitated.

Figure 14:
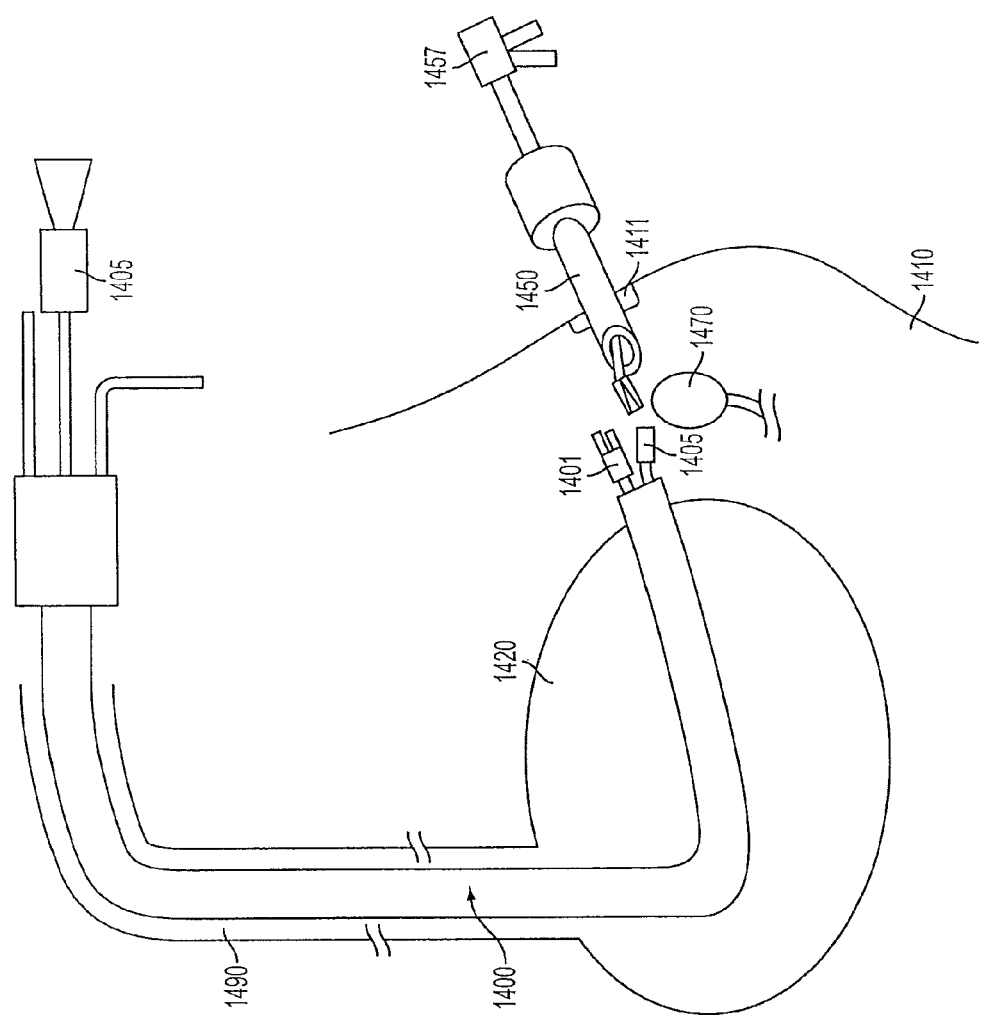
FIG. 14 is a schematic representation of a cholecystectomy in accordance with the invention.

The present invention also relates to surgical procedures performed utilizing devices set forth herein. FIG. 14 illustrates an endoluminal and transluminal access device 1400 being used in a trans-gastric cholecystectomy (removal of gall bladder). As illustrated, the access device 1400 is inserted by way of the esophagus 1490 of a patient, into the stomach 1420 of the patient. Access is made by way of an incision through the wall of the stomach 1420, into the abdominal cavity 1410. An incision is made in any suitable manner, but preferably by an endoscopic cutting implement placed through the lumen of the access device 1400, which induces coagulation, such as by electrocautery or ultrasonic vibrations.

Either preceding or following this step, a second access device 1450 is inserted through the navel or umbilicus 1411 of the patient. This mode of external access obscures any scarring that may occur. Naturally, the trans-esophageal entry of the access device 1400 carries no risk of visible scarring.

Prior to or upon entering the abdominal cavity 1410, the cavity may be insufflated by way of the access device 1400. Alternatively, the abdominal cavity can be insufflated by way of the second access device 1450 and/or still another element, such as a veress needle.

In the illustrated embodiment, a flexible endoscope 1405 is inserted through the transluminal access device 1400. Any number of additional instruments that can physically fit through the lumen of the access device 1400 can be inserted therethrough, and the fluid seal formed by the access device 1400 will maintain a seal around the instruments. An entire cholecystectomy can be performed via this access device 1400. At present it is more effective to close the incision made in the stomach wall by accessing the stomach 1420 from the outside, and for this reason, the second access device 1450 is used with a surgical stapler 1457 to close the incision made in the stomach. Therefore, the second access device 1450 is also used during the cholecystectomy. Through the channel of the second access device, an endoscope, grasper shears or any other necessary instrument can be inserted.

Upon severing the cystic duct, vascular tissue and connecting tissue, the gall bladder can be removed by either the transluminal access device 1400 or the second access device 1450. If necessary, the gall bladder can be separated into smaller pieces for removal, as by a morcellator or the like.

In accordance with one embodiment of the invention, a method for performing a cholecystectomy includes the steps of:
  Inserting a first access device in accordance with the invention through the esophagus of a patient and into the stomach;
  Penetrating the stomach wall and extending the first access device through the stomach wall;
  Inserting a second access device through the umbilicus of the patient;
  Inserting an endoscope through the first access device;
  Retracting the gallbladder with the at least one grasper;
  Exposing the cystic duct and cystic artery;
  Applying at least two clips on each of the cystic duct and artery;
  Transecting each of the cystic duct and artery with surgical scissors or another suitable instrument;
  Dissecting and removing the gallbladder from the liver bed; and
  Removing the gallbladder.

In accordance with this method, the second access device can have, for example, a diameter of 21 mm. The endoscope can be flexible and can have a diameter, for example, of about 10 mm. The cystic duct and artery can be exposed with dissectors, such as 5 mm dissectors. One or more graspers can be inserted through the second access device to manipulate the gallbladder. Clips can be applied with a 5 mm clip applier. The scissors can be 5 mm scissors, for example. Dissecting and removing the gallbladder can be accomplished with shears, such as ultrasonic shears. The gallbladder can be removed through the second access device. Alternatively, the gallbladder can be removed from the first access device, and can be removed from either access device whole or morcellated.

Figure 15:
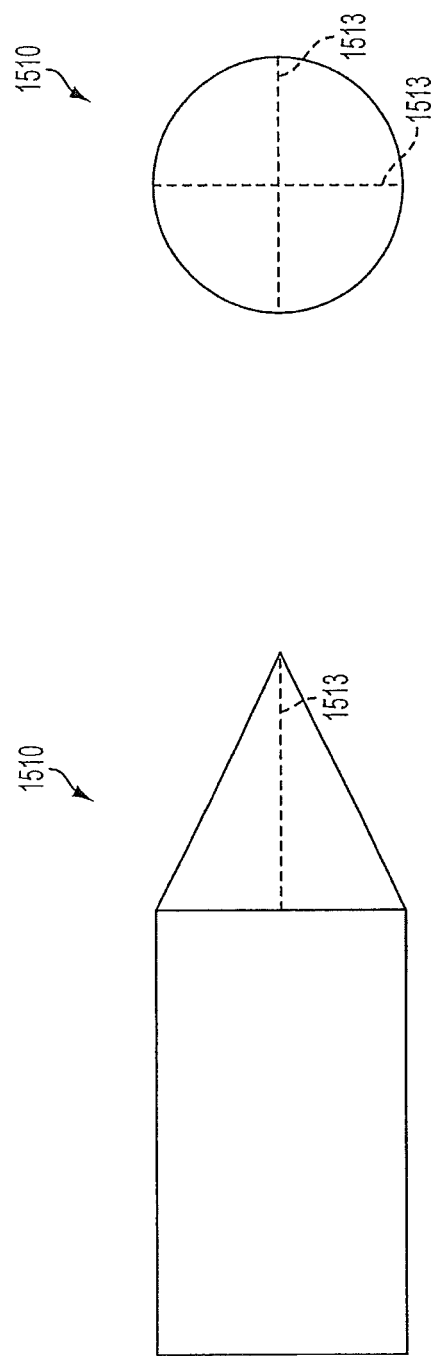
FIG. 15 are side and end views of a frangible tip in accordance with the invention.

FIG. 15 illustrates one embodiment of a distal end portion of an access device in accordance with the invention. The access device of FIG. 15 includes a frangible tip 1510 that maintains sterility of the lumen of the access device during insertion through a cavity, such as the gastrointestinal tract, until a point when the tip is ruptured or intentionally cut. The frangible tip may have any shape, and may include lines of weakness 1513, such as regions of decreased material thickness or score lines.

Having a sealed tip, instruments, such as endoscopes inserted through the access device benefit from a sterile path essentially the entire way to the surgical site. This reduces or eliminates any problems in sterilizing equipment, such as endoscopes with working channels. Advantageously, utilizing access devices in accordance with the invention eliminates the need for using endoscopes with integral working channels, because instruments can be inserted in parallel with the endoscope while maintaining a seal around all instruments. Even though sterility using access devices in accordance with the invention is enhanced as compared with simply inserting such instruments through a particular bodily opening, by including a sealed tip, sterility of a working channel is further enhanced.

Other types of tips or seals can be provided at the distal end of access devices in accordance with the invention, such as a removable cap, a sheath capable of being remotely withdrawn proximally, away from the distal tip or hinged hemispheric shutters, that function similarly to an eyelid and close over the distal opening of the lumen.

In accordance with the invention, transluminal access can be made through the rectum, colon, stomach (as illustrated in FIG. 14), esophagus or vagina, for example. Instruments that can be inserted through access devices in accordance with the invention include, but are not limited to dissectors, clip appliers, shears, automatic suturing devices, endoscopes, graspers, morcellators, suction tubes, electrocautery or coagulation devices, specimen retrieval tools, surgical staplers, as well as specialized tools for specific procedures.

Surgical procedures which may be performed with devices set forth herein, and in accordance with methods set forth herein include: cholecystectomy, appendectomy bariatric procedures, such as adjustable gastric banding (lap band), gastrectomy, such as sleeve gastrectomy, any of a variety of procedures to alleviate gastroesophageal reflux disease (GERD), tubal ligation, oophorectomy, nephrectomy, prostatectomy, colorectal procedures, hernia repair, gynecological resection, resection of the spleen, and splenectomy.

Such procedures, as well as others applicable in accordance with the invention, can mitigate damage caused by or aide recovery from such conditions as obesity, diabetes, gastroesophageal reflux disease (GERD), gallstones, appendicitis, colon disease, ideopathic thrombocytopenia purpura (ITP) and other diseases.

It should be noted that features described and/or illustrated in connection with one embodiment described herein can be combined with or substituted for other features described and/or illustrated in connection with any other embodiment set forth herein. Although a feature may be described in one particular embodiment, it should be understood that such a feature is not limited to being provided precisely in that manner or only in that embodiment.

The access devices and related methods of the present invention, as described above and shown in the drawings, provide, among other things, access devices with superior properties including the capability to provide substantially frictionless sealing of instruments passing therethrough. Endoluminal and transluminal procedures advantageously require less time for recovery than traditional procedures, among other benefits. It will be apparent to those skilled in the art that various modifications and variations can be made in the device and method of the present invention without departing from the spirit or scope of the invention.

What is claimed is:

1. An access device adapted and configured to be inserted into a natural lumen of a patient's body through a natural orifice to gain access to a surgical site in a body cavity through a wall of the natural lumen, the access device comprising:
   a) a proximal housing portion;
   b) an elongated flexible body portion extending distally from the proximal housing portion, the flexible body portion dimensioned and configured for transluminal access to the surgical site and having a tubular wall defining a central lumen to accommodate passage of surgical instruments to the surgical site, wherein a distal end portion of the flexible body portion has a longitudinal slit formed therein extending proximally from a distal end of the body portion to gain access to the wall of the natural lumen, wherein the tubular wall forming the longitudinal slit includes laterally opposed side grasping elements configured for actuated movement between open, closed and grasping positions to engage the wall of the natural lumen, and wherein control elements are arranged within the tubular wall adjacent to the longitudinal slit to effect actuated movement of the grasping elements; and
   c) a nozzle formed within the proximal housing portion for directing pressurized fluid into the central lumen of the flexible body portion to develop a pressure differential between a pressure at the surgical site and a pressure outside of the surgical site, the pressure differential forming a barrier to an egress of pressurized fluid from the surgical site through the central lumen of the flexible body portion, while forming a fluid seal around surgical instruments passing through the central lumen of the flexible body portion to the surgical site, wherein a pressure sensing channel is formed within the tubular wall of the flexible body portion and extends from a proximal opening in the housing portion to a distal opening in a distal end of the flexible body portion for sensing pressure within the body cavity accessed through the wall of the natural orifice, wherein the pressure within the body cavity is sensed from a sensor located externally from the access device.

2. An access device as recited in claim 1, further comprising at least one manipulating element for controlling a curvature of the flexible body portion of the access device.

3. An access device as recited in claim 1, further comprising an image sensor arranged in a distal end portion of the access device, adapted and configured to capture images of a region distal to the distal end portion of the access device.

4. An access device as recited in claim 1, further comprising one or more working channels provided in the wall of the body portion of the access device.

5. An access device as recited in claim 4, wherein one of said working channels is configured and adapted to provide irrigation to the surgical site.

6. An access device as recited in claim 4, wherein one of said working channels is configured and adapted to provide drainage from the surgical site.

7. An access device as recited in claim 1, further comprising a light source arranged in the distal end portion of the flexible body portion.

8. An access device as recited in claim 1, wherein the grasping elements are undulating grasping elements.

9. An access device as recited in claim 1, wherein the grasping elements are straight grasping elements.

10. An access device as recited in claim 1, wherein the control elements include ribs arranged in the tubular wall of the distal end portion of the flexible body portion formed from a shape memory alloy.

11. An access device as recited in claim 1, wherein the control elements include one or more control wires in the tubular wall of the distal end portion of the flexible body portion.

12. An access device as recited in claim 10, wherein the ribs formed from a shape memory alloy have a first shape at a first temperature and a second shape at a second temperature.

13. An access device as recited in claim 12, wherein resistive heating of the ribs through application of a voltage thereto causes the ribs to change from the first shape to the second shape.

14. An access device as recited in claim 12, wherein the first shape of the ribs corresponds to the grasping elements being in a closed position, and the second shape of the ribs corresponds to the grasping elements being in an open position.

* * * * *